United States Patent [19]
Edgar et al.

[11] Patent Number: 5,880,148
[45] Date of Patent: Mar. 9, 1999

[54] COMBINATION OF FENOFIBRATE AND VITAMIN E, AND METHOD OF USE OF SAME IN THERAPEUTIC TREATMENTS

[75] Inventors: Alan Dunlap Edgar, Saint-Julien; François Bellamy, Saulon-La-Rue, both of France

[73] Assignee: Laboratoires Fournier S.A., Dijon, France

[21] Appl. No.: 594,658

[22] Filed: Feb. 2, 1996

[30] Foreign Application Priority Data

Feb. 2, 1995 [FR] France .................................. 95 01216

[51] Int. Cl.$^6$ ....................... A61K 31/355; A61K 31/235
[52] U.S. Cl. ............................................. 514/458; 514/543
[58] Field of Search ................................... 514/458, 543

[56] References Cited

U.S. PATENT DOCUMENTS

| | | |
|---|---|---|
| 4,460,596 | 7/1984 | Matsumoto et al. . |
| 4,800,079 | 1/1989 | Boyer . |
| 4,895,726 | 1/1990 | Curtet et al. . |
| 5,153,001 | 10/1992 | Ismail . |
| 5,532,387 | 7/1996 | Matsui et al. . |

FOREIGN PATENT DOCUMENTS

| | | |
|---|---|---|
| 0 295 637 | 12/1988 | European Pat. Off. . |
| 0 330 532 | 8/1989 | European Pat. Off. . |
| 0 344 820 | 12/1989 | European Pat. Off. . |
| WO 94/15592 | 7/1994 | WIPO . |

OTHER PUBLICATIONS

Abstract of JP–A05 194 209—Grelan Pharm Co., Ltd, 1993.
Steinerova, A., et al., The Efficacy of Fenofibrate and alfa–Tocoferol . . . , Scandinavian Journal of Clinical Laboratory Investigation, 1995, 55, suppl. 223, abstract 623.
Hoffman, Ron, et al., Hypolipidemic Drugs Reduce Lipoprotein Susceptibility to Undergo Lipid . . . , Atherosclerosis, 93 (1992) pp. 105–113.

*Primary Examiner*—William R. A. Jarvis
*Attorney, Agent, or Firm*—Evenson, McKeown, Edwards & Lenahan P.L.L.C.

[57] ABSTRACT

The present invention relates to a novel combination of fenofibrate and a vitamin E substance which comprises:

(a) a micronized mixture of fenofibrate with a solid surfactant, and
(b) a vitamin E substance selected from the group consisting of tocopherols, their esters with organic acids, and mixtures thereof, wherein:

(1) the micronized mixture contains 33 to 200 mg of fenofibrate and the amount of said vitamin E substance represents 100 to 600 IU, and
(2) the ratio (Ra) of the amount of fenofibrate, expressed in mg, to the amount of vitamin E substance, expressed in IU, is between 0.33 and 2 mg/IU.

It further relates to the method of use of this combination in therapeutic treatments.

9 Claims, No Drawings

COMBINATION OF FENOFIBRATE AND VITAMIN E, AND METHOD OF USE OF SAME IN THERAPEUTIC TREATMENTS

BACKGROUND AND SUMMARY OF THE INVENTION

The present invention relates to a novel combination of fenofibrate and vitamin E, which is useful as an antiatheromatous drug and exhibits a synergistic effect as regards protection of plasma low density lipoproteins (LDL) from oxidation.

The present invention further relates to a method of using this novel synergistic combination in therapeutic treatments.

Vitamin E, which has the nomenclature α-tocopherol or 3,4-dihydro-2,5,7,8-tetra-methyl-2-(4,8,12-trimethyltridecyl)-2H-1-benzopyran-6-ol and has the following structural formula:

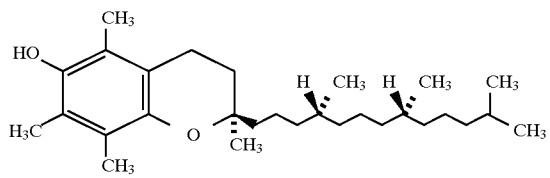

is a vitamin which has antioxidizing properties. Vitamin E is generally used either in the dl form (i.e. the so-called natural form), in the d form (i.e. the more active diastereoisomer), or in an esterified form, especially with acetic acid.

Vitamin E acetate, which is also known as α-tocopherol acetate or α-tocopheryl acetate, has the following structural formula:

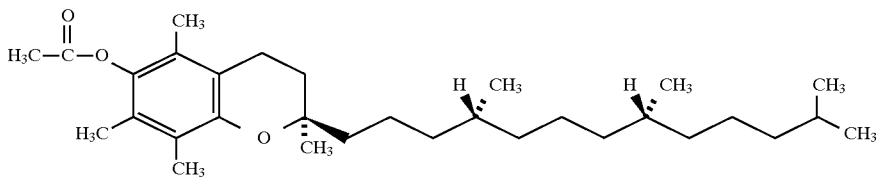

and is generally used in the dl form (i.e. the "standard" product) or the d form.

According to the *Merck Index*, (1989), 11th edition, pages 1579–1580, entries no. 9931 "Vitamin E" and no. 9932 "Vitamin E Acetate", the international unit (IU) for vitamin E is defined on the basis of dl-α-tocopherol acetate. This gives rise to the following relationships:

(1) 1 mg of dl-α-tocopherol acetate=1 IU (2) 1 mg of d-α-tocopherol acetate=1.36 IU Additionally, as liposoluble antioxidants, vitamin E and vitamin E acetate protect the plasma lipoproteins, and in particular the low density lipoproteins (LDL), from oxidation by free radicals.

Fenobibrate, which has the systematic nomenclature isopropyl 2-[4-(4-chlorobenzoyl)phenoxy]-2-methylpropionate or 2-[4-(4-chlorobenzoyl)phenoxy]-2-methylpropionic acid 1-methylethyl ester (according to *Chemical Abstracts*) and has the following structural formula:

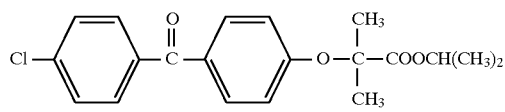

is a hypolipidemic which also lowers cholesterolemia and triglyceridemia.

U.S. Pat. No. 4,895,726, counterpart of EP-A-0 330 532 discloses a solution for improving the bioavailability of fenofibrate, herein a unit dose of 200 mg of fenofibrate, which was previously co-micronized with a solid surfactant, is therapeutically equivalent to a dose of 300 mg of fenofibrate, which was micronized in the absence of a solid surfactant.

Finally, the capacity of fenofibrate to protect lipoproteins from oxidation has been studied in the article entitled "Antioxidant Therapy and Uptake of Human oxidized LDL by Macrophages" by J. C. FRUCHART et al., *Annals of the New York Academy of Sciences*, 1989, vol. 570, pp. 447–448. According to said article, the LDL of hypercholesterolemic patients who had received 300 mg/d of fenofibrate, 1000 mg/d of vitamin E (i.e. dl-α-tocopherol) or the combined treatment of 300 mg/d of fenofibrate and 1000 mg/d of vitamin E for two months were isolated and then oxidized by incubation (24 h) with copper, before being transferred and incubated (5 h) in a culture of mouse peritoneal macrophages in order to study the uptake of LDL.

The results given in said article indicate that (i) the uptake of LDL in the group of patients who had received fenofibrate is identical to that in the control group, meaning that said fenofibrate has no effect on the oxidation of the LDL, and (ii) the rate of uptake of LDL decreases by 19.9% for the group which had received vitamin E and by 22.4% for the group which had received the fenofibrate/vitamin E combination.

It was found according to the present invention, that the incubation period of 24 h for oxidizing LDL with copper (according to J. C. FRUCHART et al.) is too long and that the results obtained are consequently rather imprecise and unreliable.

Therefore, there is a need for a novel drug for the treatment and/or prevention of atheromatous diseases.

Accordingly, the present invention relates to a combination of fenofibrate and vitamin E which is genuinely effective in protecting plasma lipoproteins in particular, especially LDL and, if appropriate, the very low density lipoproteins (VLDL), from oxidation.

The solution which is recommended for this purpose utilizes a combination of fenofibrate and vitamin E wherein:

the fenofibrate has previously been co-micronized with a solid surfactant, and the ratio Ra of the amount of fenofibrate (expressed in mg) to the amount of vitamin E (expressed in IU) is greater than 0.3 mg/IU, in contrast to the teaching of the article by J. C. FRUCHART et al. cited above.

The present invention is based on two discoveries. The first is that, while fenofibrate which has not been co-micronized with a solid surfactant has practically no protective effect on LDL plasma lipoproteins with respect to oxidation according to J. C. FRUCHART et al., fenofibrate which has been co-micronized with a solid surfactant does protect said lipoproteins from oxidation.

The second discovery is that the fenofibrate/vitamin E substance combination exhibits a synergistic effect as regards protection of lipoproteins, such as LDL, from oxidation when the following two conditions are satisfied:
(i) the fenofibrate forming part of said combination has previously been co-micronized with a solid surfactant; and
(ii) the above-mentioned ratio Ra is between 0.33 and 2 mg/IU.

According to a first feature of the present invention, a novel combination of fenofibrate and a vitamin E substance is recommended which comprises:
(a) a micronized mixture of fenofibrate with a solid surfactant, and
(b) a vitamin E substance selected from the group consisting of tocopherols, their esters with organic acids, and mixtures thereof,
with the following two conditions:
(1) said micronized mixture contains 33 to 200 mg of fenofibrate and the amount of said vitamin E substance represents 100 to 600 IU, and
(2) the ratio (Ra) of the amount of fenofibrate, expressed in mg, to the amount of said vitamin E substance, expressed in IU, is between 0.33 and 2 mg/IU.

According to a second feature of the present invention, a novel method of using said co-micronized fenofibrate/vitamin E substance combination is recommended for the preparation of a drug intended for use in therapeutics for the treatment and prevention of atheromatous diseases.

DETAILED DESCRIPTION OF A PREFERRED EMBODIMENT

In order to simplify the present description, the expression "co-micronized fenofibrate" is understood to refer to fenofibrate which has previously been co-micronized with a solid surfactant, and "non co-micronized fenofibrate" is understood to refer to fenofibrate which has been micronized in the absence of a solid surfactant.

Furthermore, in therapeutic terms, the expression "co-micronized fenofibrate/vitamin E substance combination" encompasses, according to the present invention, either a medication comprising the separate (generally simultaneous) administration of co-micronized fenofibrate and a vitamin E substance, or a medication comprising the administration of a composition containing both the active ingredients together.

"Vitamin E substance" is understood here to mean:
(i) a substance belonging to the group consisting of α-, β-, γ-, δ-, $\zeta_1$-, $\zeta_2$- and η-tocopherols, and their dl, d and l forms, where appropriate;
(ii) the corresponding esters obtained with organic acids; and
(iii) mixtures thereof.

Preferably, said vitamin E substance will be selected from dl-α-tocopherol, d-α-tocopherol, dl-α-tocopherol acetate and d-α-tocopherol acetate, the preferred vitamin E substance according to the invention being dl-α-tocopherol acetate.

When using dl-α-tocopherol acetate or when expressing the amount of any other vitamin E substance as the equivalent weight of dl-α-tocopherol acetate, the above-mentioned ratio Ra (in mg/IU) becomes a weight ratio Rw, as 1 mg of dl-α-tocopherol acetate=1 IU. When considering this weight ratio Rw, the ratio $$Rw = \frac{\text{amount of fenofibrate (mg)}}{\text{amount of vitamin E substance expressed in equivalents of dl-α-tocopherol acetate (mg)}}$$

in the co-micronized fenofibrate/vitamin E substance combination must be between 0.33 and 2 according to the present invention.

The micronized mixture of fenofibrate and solid surfactant generally contains 0.75 to 10.5 parts by weight of solid surfactant per 100 parts by weight of fenofibrate and has a particle size smaller than 15 μm, preferably smaller than or equal to 10 μm, and particularly preferably smaller than or equal to 5 μm.

The preferred solid surfactant according to the present invention is sodium laurylsulfate (LSNa), as indicated in U.S. Pat. No. 4,895,726 cited above. In practical terms, 1 to 7 parts by weight of LSNa will be used here per 100 parts by weight of fenofibrate to produce the micronized mixture.

The combination according to the present invention can be administered in any form. When the mode of administration is oral it is particularly preferable to use gelatin capsules or tablets.

In general, for the administration of the co-micronized fenofibrate/vitamin E substance combination, and in particular for the administration of the preferred co-micronized fenofibrate/dl-α-tocopherol acetate combination according to the present invention, two solutions are provided in which Ra is always between 0.33 and 2 mg/IU:
(α) the separate daily administration, in the form of gelatin capsules, of (a) 33 to 200 mg of fenofibrate co-micronized with sodium laurylsulfate in association with a physiologically acceptable excipient, and (b) 100 to 600 IU of vitamin E substance (preferably 100 to 600 mg of dl-α-tocopherol acetate) in association with a physiologically acceptable excipient; and
(β) the daily administration of a single form comprising fenofibrate co-micronized with LSNa, and the vitamin E substance, at the doses in point (α) above, in which form the vehicles of the two active ingredients are joined or placed side by side (this case is encountered especially when the single form comprises either a tablet of co-micronized fenofibrate and a tablet of vitamin E substance joined by a side or a face, or a gelatin capsule containing said co-micronized fenofibrate and said vitamin E substance together).

Posology (Dosage)

The daily recommended dosage according to the present invention consists of the oral administration of a combination of:
(a) a micronized mixture of 33 to 200 mg of fenofibrate with 0.33 to 14 mg of LSNa, and
(b) 100 to 600 mg (i.e. 100 to 600 IU) of dl-α-tocopherol acetate,
and the weight ratio Rw in this combination is between 0.33 and 2 (i.e. Ra=0.33–2 mg/IU).

It will be preferable to administer a composition containing both these ingredients in the presence of an excipient, according to the solution in point (β) above.

The combination according to the present invention is useful for the treatment and prevention of pathological conditions which involve oxidation of lipoproteins, especially atheromatous diseases, diabetes and arterial hypertension, and for the prevention of restenosis, in the sense that it reduces the plasma lipid level through the fenofibrate and that it protects the low density lipoproteins, LDL, from oxidation through the synergistic effect of co-micronized fenofibrate/vitamin E substance.

Further advantages and characteristics of the present invention will be understood more clearly from the following description of practical Examples, pharmacological results and comparative tests. Of course, this data as a whole does not imply any limitation but is given by way of illustration.

EXAMPLE 1

A combination for daily administration to adults is prepared which comprises:

a gelatin capsule of a micronized mixture (particle size smaller than or equal to 5 μm) consisting of 200 mg of fenofibrate and 4 mg of LSNa in association with a physiologically acceptable excipient, and a gelatin capsule containing 200 mg of dl-α-tocopherol acetate in association with a physiologically acceptable excipient.

Rw=1

EXAMPLE 2

A combination for daily administration to adults is prepared which comprises:

a gelatin capsule of a micronized mixture (particle size smaller than or equal to 5 μm) consisting of 200 mg of fenofibrate and 6 mg of LSNa in association with a physiologically acceptable excipient, and a gelatin capsule containing 400 mg of dl-α-tocopherol acetate in association with a physiologically acceptable excipient.

Rw=0.5

EXAMPLE 3

A combination for daily administration to adults is prepared which comprises:

a gelatin capsule of a micronized mixture (particle size smaller than or equal to 5 μm) consisting of 200 mg of fenofibrate and 6 mg of LSNa in association with a physiologically acceptable excipient, and a gelatin capsule containing 300 mg of dl-α-tocopherol acetate in association with a physiologically acceptable excipient.

Rw=0.67

EXAMPLE 4

A combination for daily administration to adults is prepared which comprises a single form consisting of two tablets joined side by side, one containing a micronized mixture (particle size smaller than or equal to 5 μm) of 200 mg of fenofibrate and 8 mg of LSNa in association with a physiologically acceptable excipient, and the other containing 290 mg of dl-α-tocopherol acetate in association with a physiologically acceptable excipient.

Rw=0.69

EXAMPLE 5

Gelatin capsules were prepared which each contain a micronized mixture (particle size smaller than or equal to 5 μm) consisting of 100 mg of fenofibrate and 3 mg of LSNa, mixed with 150 mg of dl-α-tocopherol acetate, in association with a physiologically acceptable excipient, wherein the daily dose administered to adults corresponded to 2 gelatin capsules.

Rw=0.67

EXAMPLE 6

A combination for daily administration to adults is prepared which comprises:

a gelatin capsule of a micronized mixture (particle size smaller than or equal to 5 μm) consisting of 200 mg of fenofibrate and 6 mg of LSNa in association with a physiologically acceptable excipient, and a gelatin capsule containing 100 mg of dl-α-tocopherol acetate in association with a physiologically acceptable excipient.

Rw=2

EXAMPLE 7

A combination for daily administration to adults is prepared which comprises:

a gelatin capsule of a micronized mixture (particle size smaller than or equal to 5 μm) consisting of 200 mg of fenofibrate and 6 mg of LSNa in association with a physiologically acceptable excipient, and two gelatin capsules each containing 300 mg of dl-α-tocopherol acetate in association with a physiologically acceptable excipient.

Rw=0.33

PHARMACOLOGICAL AND COMPARATIVE TESTS

Tests were performed on adult male WISTAR rats weighing about 230 g, using 5 or 6 animals per group and per test product or combination. Each animal received oral administration (gastric intubation) for 3, 8, 15 or 27 days, of either soya oil (2 ml/kg/d), or (i) co-micronized fenofibrate (3 parts by weight of LSNa per 100 parts by weight of fenofibrate, as indicated in Example 5 above) or non co-micronized fenofibrate, (ii) dl-α-tocopherol acetate, or (iii) mixtures thereof, dissolved or suspended in the same amount of soya oil (2 ml/kg/d).

The animals in each group received one of the following treatments:

(A) soya oil (control group);
(B) 37 mg/kg/d of co-micronized fenofibrate in soya oil;
(C) 55 mg/kg/d of dl-α-tocopherol acetate in soya oil; or
(D) a combination of 37 mg/kg/d of co-micronized fenofibrate according to (B) and 55 mg/kg/d of dl-α-tocopherol acetate according to (C) [Rw=0.67] in soya oil.

Throughout each test, the animals had free access to food and drinking water. At the end of each test (3, 8, 15, 27 days), the rats received the last dose and were then deprived of food. 5 hours later, the animals were anesthetized with pentobarbital sodium and blood was then taken, from the abdominal aorta, on EDTA (1 mg/ml). The plasmata were subsequently separated off by centrifugation at reduced speed and then frozen at a temperature of −20° to −70° C. for analyses at a later stage.

In a first series, the plasma levels of total cholesterol, phospholipids and triglycerides were evaluated. The results obtained, which are collated in Table I below, show that fenofibrate administered on its own causes a significant decrease in the total plasma cholesterol (variation from −31 to −40%), very slightly reduces the plasma phospholipid levels and does not modify the plasma triglyceride levels.

When combined with dl-α-tocopherol acetate, fenofibrate generates the same changes, whereas dl-α-tocopherol acetate administered on its own is inactive.

The results in Table I, which are the mean (n=6)±the root-mean-square error, are therefore consistent with the previously disclosed effects of fenofibrate and dl-α-tocopherol acetate on the plasma levels of total cholesterol, phospholipids and triglycerides.

In a second series, the protection of all the LDL and VLDL lipoproteins from oxidation was evaluated by following the kinetics of formation of conjugated dienes.

For this purpose, the fraction containing LDL and VLDL was separated off by ultracentrifugation using a device comprising a fixed-angle rotor. To do this, the density of the plasma was increased to 1.050 g/ml by the addition of solid KBr; the plasma (4 ml) was then covered with 4 ml of a solution containing NaCl (9 mg/ml), EDTA (1 mg/ml) and KBr (to a density of 1.050 g/ml) and ultracentrifuged (45,000 rpm; 15° C.; 22 h) using a BECKMAN 50 Ti device; the supernatant was collected and kept in the dark at 4° C. under a nitrogen atmosphere. Each resulting sample of supernatant was dialyzed at 4° C. and in the dark against 2×5 l of phosphate-buffered saline (PBS) containing 10 μM EDTA, and then for 4 h against PBS on its own (to remove the KBr and EDTA). The lipoproteins (LDL+VLDL mixture) isolated in this way were incubated at 37° C. in 1 ml of PBS containing 5 μM CuSO$_4$, for at most 10 hours, and the oxidation resistance was followed by recording the variation in absorbance at 234 nm, relative to the initial absorbance without CuSO$_4$ treatment, every 10 minutes during incubation. The results obtained show that, in contrast to the teaching of J. C. FRUCHART et al. (i.e. 24 h of incubation), 5 h of incubation are sufficient in this case.

The results relating to protection of the lipoproteins (LDL and VLDL) from oxidation are collated in Table II below, in which the propagation rate is the slope of the linear segment portion of the propagation phase, and the lag time, or lag phase time, is the intersection of this linear segment portion with the time axis on the abscissa.

The propagation rate is expressed here as $$\frac{\Delta \text{ absorbance}}{\text{minute}} \times 1000$$

and the lag time is expressed in minutes.

The results in Table II are the mean (n=6, unless indicated otherwise)±the root-mean-square error. It shows that the co-micronized fenofibrate/vitamin E substance combination according to the present invention exhibits a synergistic effect.

TABLE I

| TREATMENT | DURATION (days) | (1) | (2) | (3) |
|---|---|---|---|---|
| A) Soya oil (control) | 3 | 0.81 ± 0.03 | 1.33 ± 0.03 | 0.65 ± 0.10 |
| B) Co-micronized fenofibrate (37 mg/kg/d) | 3 | 0.49 ± 0.02★ | 0.97 ± 0.02★ | 0.44 ± 0.03 |
| C) dl-α-Tocopherol acetate (55 mg/kg/d) | 3 | 0.74 ± 0.03★ | 1.28 ± 0.04 | 0.72 ± 0.10 |
| D) B + C | 3 | 0.52 ± 0.02★ | 1.02 ± 0.01★ | 0.51 ± 0.03 |
| A) Soya oil (control) | 8 | 0.67 ± 0.02 | 1.25 ± 0.04 | 0.83 ± 0.09 |
| B) Co-micronized fenofibrate (37 mg/kg/d) | 8 | 0.46 ± 0.02★ | 1.09 ± 0.02★ | 0.43 ± 0.05 |
| C) dl-α-Tocopherol acetate (55 mg/kg/d) | 8 | 0.69 ± 0.02 | 1.18 ± 0.05 | 0.69 ± 0.10 |
| D) B + C | 8 | 0.43 ± 0.01★ | 1.06 ± 0.02★ | 0.57 ± 0.10 |
| A) Soya oil (control) | 15 | 0.66 ± 0.04 | 1.26 ± 0.04 | 0.82 ± 0.12 |
| B) Co-micronized fenofibrate (37 mg/kg/d) | 15 | 0.4i ± 0.02★ | 1.23 ± 0.02 | 0.69 ± 0.05 |
| C) dl-α-Tocopherol acetate (55 mg/kg/d) | 15 | 0.65 ± 0.04 | 1.30 ± 0.06 | 0.86 ± 0.08 |
| D) B + C | 15 | 0.39 ± 0.02★ | 1.23 ± 0.04 | 0.71 ± 0.08 |
| A) Soya oil (control) | 27 | 0.70 ± 0.04 | 1.46 ± 0.05 | 1.16 ± 0.05 |
| B) Co-micronized fenofibrate (37 mg/kg/d) | 27 | 0.43 ± 0.02★ | 1.29 ± 0.04 | 1.24 ± 0.23 |
| C) dl-α-Tocopherol acetate (55 mg/kg/d) | 27 | 0.65 ± 0.03 | 1.35 ± 0.05 | 0.94 ± 0.11 |
| D) B + C | 27 | 0.41 ± 0.05★ | 1.30 ± 0.07 | 0.99 ± 0.11 |

Notes:
(1) Total cholesterol (g/l)
(2) Phospholipids (g/l)
(3) Triglycerides (g/l)
(★) statistically significant
(p ≤ 0.05)

TABLE II

| TREATMENT | DURATION (a) | LAG TIME (b) | PROPAGATION RATE (c) |
|---|---|---|---|
| A) Soya oil (control) | 3 | 39.2 ± 3.5 | 13.0 ± 0.4 |
| B) Co-micronized fenofibrate (37 mg/kg/d) | 3 | 54.2 ± 4.7 (n = 5) | 8.3 ± 0.2 (n + 5)★ |
| C) dl-α-Tocoperol acetate (55 mg/kg/d) | 3 | 51.8 ± 2.9 (n = 5) | 12.2 ± 0.4 (n = 5) |
| D) B + C | 3 | 73.7 ± 7.9★ | 8.0 ± 0.3★ |
| A) Soya oil (control) | 8 | 46.9 ± 2.8 | 14.1 ± 0.3 |
| B) Co-micronized fenofibrate (37 mg/kg/d) | 8 | 128.4 ± 9.0★ | 6.3 ± 0.3★ |

TABLE II-continued

| TREATMENT | DURATION (a) | LAG TIME (b) | PROPAGATION RATE (c) |
|---|---|---|---|
| C) dl-α-Tocopherol acetate (55 mg/kg/d) | 8 | 57.6 ± 3.4 | 12.4 ± 0.7★ |
| D) B + C | 8 | 155.3 ± 8.3★ | 6.0 ± 0.4★ |
| A) Soya oil (control) | 15 | 46.1 ± 3.5 | 14.6 ± 0.7 |
| B) Co-micronized fenofibrate (37 mg/kg/d) | 15 | 148.3 ± 11.0★ | 7.6 ± 0.4★ |
| C) dl-α-Tocopherol acetate (55 mg/kg/d) | 15 | 62.8 ± 4.5★ | 12.7 ± 0.9★ |
| D) B + C | 15 | 226.1 ± 25.6★ | 5.4 ± 0.3★ |
| A) Soya oil (control) | 27 | 58.0 ± 2.4 | 14.8 ± 0.5 |
| B) Co-micronized fenofibrate (37 mg/kg/d) | 27 | 139.8 ± 3.4★ | 8.4 ± 0.5★ |
| C) dl-α-Tocopherol acetate (55 mg/kg/d) | 27 | 67.4 ± 9.1★ | 11.9 ± 0.4★ |
| D) B + C | 27 | 206.6 ± 16.6★ | 6.3 ± 0.2★ |

Notes:
(a) in days
(b) in minutes
(c) as (Δ absorbance/minute) × 1000
(★) statistically significant
($p \leq 0.05$)

What is claimed is:

1. A combination of fenofibrate and a vitamin E substance which comprises:
   (a) a micronized mixture of fenofibrate with a solid surfactant, and
   (b) an amount of a vitamin E substance selected from the group consisting of tocopherols, their esters with organic acids, and mixtures thereof,
   wherein:
   (1) said micronized mixture contains 33 to 200 mg of fenofibrate and the amount of said vitamin E substance represents 100 to 600 IU, and
   (2) the ratio (Ra) of the amount of fenofibrate, expressed in mg, to the amount of said vitamin E substance, expressed in IU, is between 0.33 and 2 mg/IU.

2. The combination according to claim 1, wherein the micronized mixture of fenofibrate and solid surfactant comprises 0.75 to 10.5 parts by weight of solid surfactant per 100 parts by weight of fenofibrate.

3. The combination according to claim 1, wherein the micronized mixture of fenofibrate and solid surfactant comprises 1 to 7 parts by weight of solid surfactant per 100 parts by weight of fenofibrate.

4. A method of treating a pathological condition which involves oxidation of lipoproteins in a patient in need thereof, comprising administering to the patient an effective amount of a drug comprising a combination of fenofibrate and a vitamin E substance selected from the group consisting of tocopherols, their esters with organic acids, and mixtures thereof,
   wherein the fenofibrate of said combination is in the form of a micronized mixture with a solid surfactant, wherein:
   said micronized mixture contains 33 mg to 200 mg of fenofibrate and the amount of said vitamin E substance represents 100 IU to 600 IU, and
   the ratio of the amount of fenofibrate, expressed in mg, to the amount of said vitamin E substance, expressed in IU, is between 0.33 mg/IU and 2 mg/IU.

5. The method according to claim 4, wherein the micronized mixture of fenofibrate and solid surfactant comprises 0.75 to 10.5 parts by weight of solid surfactant per 100 parts by weight of fenofibrate.

6. The method according to claim 4, wherein the micronized mixture of fenofibrate and solid surfactant comprises 1 to 7 parts by weight of solid surfactant per 100 parts by weight of fenofibrate.

7. The method according to claim 4, wherein said vitamin E substance is selected from dl-α-tocopherol, d-α-tocopherol, dl-α-tocopherol acetate and d-α-tocopherol acetate.

8. The method according to claim 4, wherein said vitamin E substance is dl-α-tocopherol acetate.

9. The method according to claim 4 wherein the pathological condition is selected from the group consisting of at least one of atheromatous diseases, diabetes, aterial hypertension and restenosis.

* * * * *